Dec. 14, 1954 C. THOMASON Plant Pat. 1,329
PEACH TREE
Filed April 15, 1954
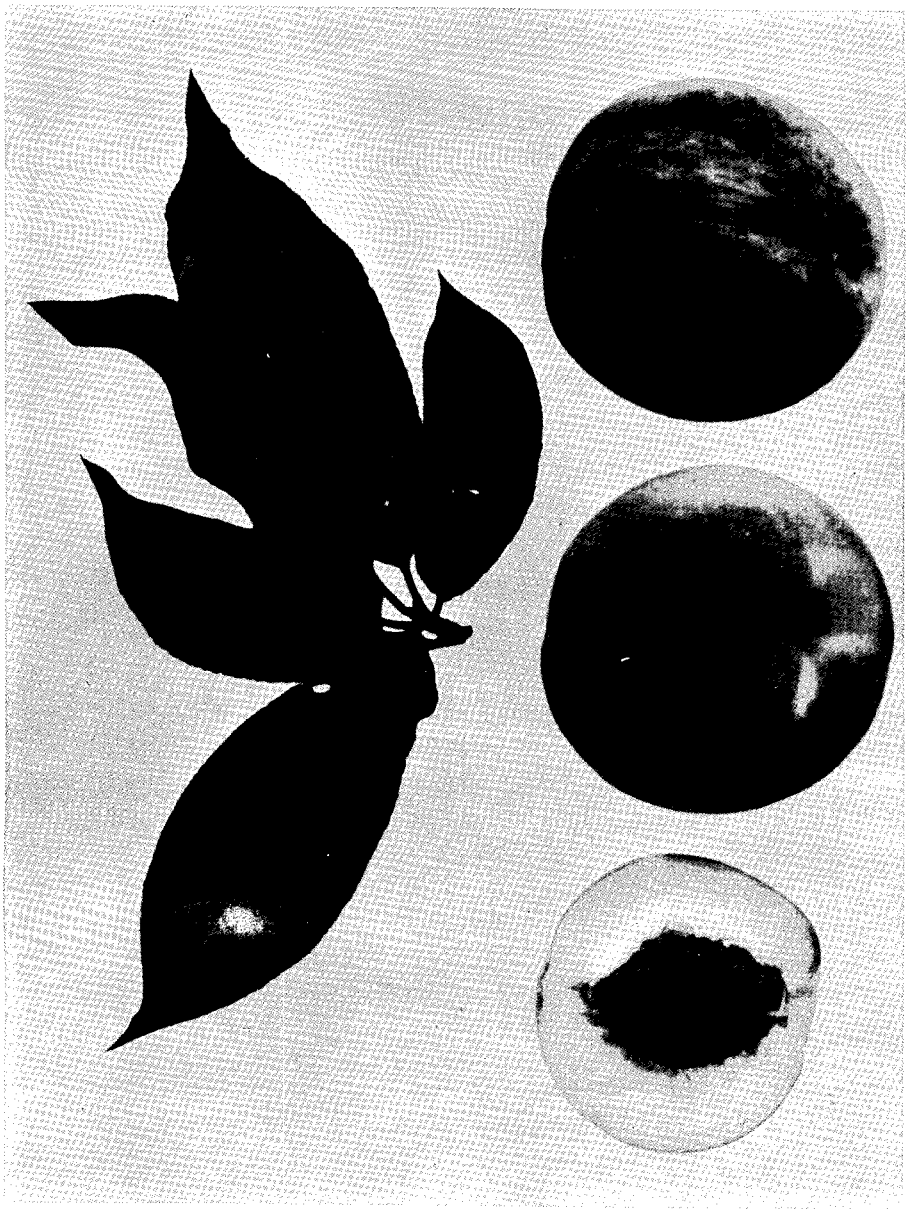
Inventor
Charles Thomason
By Robb & Robb
Attorneys United States Patent Office Plant Pat. 1,329
Patented Dec. 14, 1954

1,329

PEACH TREE

Charles Thomason, Bangor, Ala., assignor to Stark Bro's Nurseries and Orchards Company, Louisiana, Mo., a corporation of Missouri Application April 15, 1954, Serial No. 423,550

1 Claim. (Cl. 47—62)

The present invention relates to a new and distinct variety of peach tree which was originated by me by crossing the variety "Hal-Berta Giant" (Plant Patent No. 7) with an unnamed and unpatented variety identified as "New Jersey 133."

As the result of this cross, I have produced a new variety of peach of the yellow-fleshed freestone type, the fruit of which is particularly characterized as to novelty by its relatively early-ripening and slow-softening habits, combined with superior handling and shipping qualities of the fruit, and by a superior disease resistance of the new variety.

The fruit of my new variety ripens approximately fifteen days earlier than that of the variety "Elberta" (unpatented). The new variety has shown no evidence of disease from the time it was originated, to date, and tests conducted in both Blount County, Alabama, and Pike County, Illinois, show that my new variety is especially resistant to *Xanthomonas pruni,* as evidenced by the absence of leaf spot, twig cankers or other fruit infections, as well as very resistant to brown rot, all during the same period when the varieties "July Elberta" (Plant Patent No. 15) and "J. H. Hale" (unpatented), growing in the same areas and under the same cultural conditions, were very severely damaged by *Xanthomonas pruni* in Blount County, Alabama, and over half of the crops of the varieties "Hale Haven" (unpatented), "Erly Red Fre" (Plant Patent No. 320), "Early Rose" (unpatented), "Alton" (unpatented), and "Fair's Beauty" (unpatented) were destroyed by brown rot in Blount County, Alabama. My new variety has shown no evidence whatsoever of disease in Pike County, Illinois, while the varieties "J. H. Hale," "July Elberta" and many others have been severely damaged in that area.

The foregoing characteristics and distinctions definitely differentiate my new variety from its parents, as well as from all other varieties of its class.

Asexual reproduction of my new variety by budding in test orchards near Atlas, Pike County, Illinois, shows that the foregoing characteristics and distinctions come true to form and are established and transmitted through succeeding propagations.

The accompanying drawing shows typical specimens of the fruit and foliage of my new variety, with the fruit shown in elevation, as well as in cross-section to expose the stone.

The following is a detailed description of my new variety, with color terminology in accordance with Ridgway's Color Standards and Nomenclature and with the Horticultural Color Guide, as indicated, and as based upon observations made from specimens grown in test orchards near Atlas, Pike County, Illinois:

Dates of first and last picking: August 10th–August 14th.
Tree: Medium size; vigorous; open; spreading; vase-formed; hardy; productive; regular bearer.
*Trunk.*—Medium stocky.
*Branches.*—Medium stocky; smooth.
Color—Russet, Plate XV, Color No. 13, Tone K (Ridgway).
Lenticels—From few to medium number; from small to medium size.
*Leaves.*—Thick; smooth.
Length—4⅞ inches.
Width—1⅝ inches.
Size—Medium.
Shape—Oval; acutely pointed.

Color—Spinach Green, Colour No. o960, page 187, volume 2 (Horticultural Color Guide).
Margin—Glandular; finely serrate.
Petiole—Medium length; thick.
Glands—Average number 2; opposite; medium size; reniform; free.
Flowers: Between early and late, as compared with other varieties.
*Color.*—Rhodamine Pink, Colour No. 527/2, page 138, volume 2 (Horticultural Color Guide).
*Size.*—Small.
Fruit:
*Maturity when described.*—Eating-ripe.
Date—August 14th.
*Size.*—Uniform; medium.
Axial diameter—2½ inches.
Transverse diameter in suture plane—2½ inches.
Diameter at right angles to suture plane—2⅜ inches.
*Form.*—Variable; unsymmetrical; globose; compressed laterally towards suture.
*Suture.*—Distinct; shallow; extends from base beyond apex; has slight marked depression beyond pistil point.
*Ventral surface.*—Slightly lipped toward apex; lips equal.
*Cavity.*—Abrupt; elongated, with suture showing on one side; depth 9/16 inch; breadth 1 inch.
*Base.*—Truncate; oblique.
*Apex.*—Rounded to depressed; apical.
*Stem.*—3/16 inch long; stout; pubescent; medium adherence to stone.
*Skin.*—Medium thickness; tough; tenacious to flesh; no tendency to break in wet or dry seasons; moderate, medium short down; down rolls up when rubbed.
Color—Highly blushed with Chrysanthemum Crimson, Colour No. 824/1, page 169, volume 2 (Horticultural Colour Guide).
*Flesh.*—Color—Buttercup Yellow, Colour No. 5/2, page 5, volume 1 (Horticultural Color Guide), with greenish tinge, and streaked with Carmine, Colour No. 21/1, page 21, volume 1 (Horticultural Color Guide) next to stone; surface of pit cavity Carmine, Colour No. 21/1, page 21, volume 1 (Horticultural Color Guide).
Amygdalin—Wanting.
Juice—Moderate; rich.
Texture—Meaty.
Fibers—Few; fine; tender.
Ripens—Fairly even.
Flavor—Sub-acid; vinous.
Aroma—Distinct.
Eating quality—Best.
*Stone.*—Free; with short fibers parting smoothly from flesh.
Size—Medium.
Length—1⅜ inches.
Thickness—11/16 inch.
Form—Oval; full toward apex.
Base—Oblique; narrow; oval.
Apex—Acute.
Sides—Unequal; curved on right side.
Surface—Irregularly furrowed throughout; pitted throughout.
Ridges—Ragged toward apex.
Pits—Elongated.
Ventral edge—Thin; with wing throughout.
Dorsal edge—Narrow; with shallow, narrow groove throughout; interrupted ridges on either side.
*Disease resistance.*—Good; especially resistant to brown rot and to *Xanthomonas pruni,* showing no leaf spot, twig cankers or other fruit infections in Blount County, Alabama, and in Pike County, Illinois, and very few instances of any brown rot in Blount County, Alabama, as compared with other varieties grown in the same areas under the same cultural conditions.
*Use.*—Market; dessert; canning.
*Keeping quality.*—Medium.

*Shipping quality.*—Good.

I claim:

A new and distinct variety of peach tree of the yellow-fleshed freestone class, substantially as herein shown and described, characterized particularly as to novelty by the relatively early-ripening and slow-softening habits of its fruit, by the superior handling and shipping qualities of its fruit, and by its superior disease resistance.

No references cited.